(12) United States Patent
Kitamura et al.

(10) Patent No.: US 11,866,611 B2
(45) Date of Patent: Jan. 9, 2024

(54) PLASMA SPRAY MATERIAL

(71) Applicant: TOMITA PHARMACEUTICAL CO., LTD., Naruto (JP)

(72) Inventors: Naoyuki Kitamura, Naruto (JP); Akihito Bando, Naruto (JP); Yuta Tsumura, Naruto (JP); Shota Minami, Naruto (JP)

(73) Assignee: TOMITA PHARMACEUTICAL CO., LTD., Naruto (JP)

( * ) Notice: Subject to any disclaimer, the term of this patent is extended or adjusted under 35 U.S.C. 154(b) by 772 days.

(21) Appl. No.: 16/770,030

(22) PCT Filed: Dec. 6, 2018

(86) PCT No.: PCT/JP2018/044900
§ 371 (c)(1),
(2) Date: Jun. 4, 2020

(87) PCT Pub. No.: WO2019/112001
PCT Pub. Date: Jun. 13, 2019

(65) Prior Publication Data
US 2020/0347239 A1    Nov. 5, 2020

(30) Foreign Application Priority Data

Dec. 8, 2017   (JP) ................ 2017-236440

(51) Int. Cl.
*C23C 4/134*    (2016.01)
*C09D 1/00*     (2006.01)
(Continued)

(52) U.S. Cl.
CPC ............ *C09D 5/032* (2013.01); *A61L 27/06* (2013.01); *A61L 27/32* (2013.01); *A61L 27/56* (2013.01);
(Continued)

(58) Field of Classification Search
CPC ........................................ C23C 4/134
See application file for complete search history.

(56) References Cited

U.S. PATENT DOCUMENTS 5,128,146 A    7/1992  Hirayama et al.
5,211,661 A    5/1993  Shinjou et al.
(Continued)

FOREIGN PATENT DOCUMENTS

CA    2779103 A1 * 5/2011  ............... A61F 2/28
CN    101591759 A    12/2009
(Continued)

OTHER PUBLICATIONS

Yip et al. Thermal Spraying of Ti—6Al—4V hydroxyapatite composites coatings: powder processing and post-spray treatment Journal of Materials Processing Technology 65. 73-79. 1997 (Year: 1997).*

(Continued)

*Primary Examiner* — Cachet I Proctor
(74) *Attorney, Agent, or Firm* — Knobbe Martens Olson & Bear LLP

(57) ABSTRACT

The purpose of the present invention is to provide a plasma spray material which is capable of forming a hydroxyapatite film that exhibits high adhesion strength with respect to substrates such as metal substrates. When used as a plasma spray material, hydroxyapatite powder having a modal diameter of 550-1000 nm in a pore diameter of at most 5000 nm as measured by a mercury intrusion method is capable of forming a hydroxyapatite film that exhibits high adhesion strength with respect to substrates such as metal substrates.

17 Claims, 9 Drawing Sheets

(51) Int. Cl.
*C09D 5/03* (2006.01)
*A61L 27/06* (2006.01)
*A61L 27/32* (2006.01)
*A61L 27/56* (2006.01)
*C01B 25/32* (2006.01)
*C23C 4/04* (2006.01)

(52) U.S. Cl.
CPC ............... *C01B 25/32* (2013.01); *C09D 1/00* (2013.01); *C09D 5/031* (2013.01); *C23C 4/04* (2013.01); *C23C 4/134* (2016.01); *A61L 2420/02* (2013.01); *A61L 2430/24* (2013.01); *C01P 2002/72* (2013.01); *C01P 2004/02* (2013.01); *C01P 2004/61* (2013.01); *C01P 2006/11* (2013.01); *C01P 2006/14* (2013.01); *C01P 2006/16* (2013.01)

(56) References Cited

U.S. PATENT DOCUMENTS

| | | | |
|---|---|---|---|
| 2005/0169956 A1* | 8/2005 | Erbe | A61L 27/58 424/602 |
| 2005/0288795 A1* | 12/2005 | Bagga | A61L 27/54 606/92 |
| 2008/0206554 A1 | 8/2008 | Riman et al. | |
| 2012/0052183 A1* | 3/2012 | Wu | C23C 4/134 427/2.1 |
| 2013/0078476 A1 | 3/2013 | Riman et al. | |
| 2016/0166386 A1 | 6/2016 | Gerber et al. | |
| 2016/0256607 A1* | 9/2016 | Francis | A61L 27/3834 |
| 2020/0031669 A1 | 1/2020 | Minami et al. | |

FOREIGN PATENT DOCUMENTS

| | | |
|---|---|---|
| JP | S63-093851 A | 4/1988 |
| JP | H02-140171 A | 5/1990 |
| JP | H10-001375 A | 1/1998 |
| JP | H101375 A * | 1/1998 |
| JP | 2016-138309 A | 8/2016 |
| JP | 6164628 B1 | 7/2017 |
| WO | WO 87/06843 A1 | 11/1987 |
| WO | WO 2011/053598 A1 | 5/2011 |

OTHER PUBLICATIONS

Bastan et al. Spray drying of hydroxyapatite powders: The effect of spray drying parameters and heat treatment on the particle size and morphology Journal of Alloys and Compounds. 724. 2017. pp. 586-596 (Year: 2017).*

Chinese Office Action issued in Chinese Patent Application No. 201880078351.0 dated Dec. 2, 2021.

English Translation of ISR of PCT/JP2018/044900, mailed Jan. 29, 2019.

Supplementary European Search Report in EP Patent Application No. 18 88 4898.0 dated Feb. 26, 2021.

* cited by examiner

FIG. 2

| Test specimen | Magnification: ×500 | Magnification: ×10000 |
|---|---|---|
| Example 4 | | |
| Comparative Example 3 | | |
| Comparative Example 4 | | |
| Comparative Example 5 | | |
| Comparative Example 6 | | |
| Comparative Example 7 | | |
| Comparative Example 8 | | |

| Test specimen | Magnification: ×500 | Magnification: ×1000 |
|---|---|---|
| Comparative Example 3 |  |  |
| Comparative Example 7 |  |  |
| Comparative Example 8 |  |  |

# PLASMA SPRAY MATERIAL

TECHNICAL FIELD

The present invention relates to a plasma spray material capable of forming a hydroxyapatite film having a high adhesive strength to a substrate such as a metal substrate.

BACKGROUND ART

In recent years, fractures and coxarthrosis caused by aging increase, and artificial joints have increasingly been used.

As the artificial joint, a metal substrate such as a titanium alloy or a cobalt alloy having high strength and stability is used. However, it is generally known that although metal substrates used in artificial joints show compatibility with a living body, the metal substrates have poor biocompatibility and are hardly adaptable to living tissues, so that a material with higher biocompatibility is coated on a surface of the substrate.

Conventionally, in order to increase the biocompatibility of artificial joints, artificial joints have been developed in which a biocompatible material such as hydroxyapatite (hereinafter sometimes referred to as HAp) or bioglass is coated on a metal substrate surface (for example, see Patent Document 1). In the production of such an artificial joint, a biocompatible material is coated by an immersion method, an electrophoresis method, a plasma spraying method, or the like, and the plasma spraying method is most widely used. A principle of the plasma spraying method is as follows. When a working gas such as an argon gas is supplied to an arc generated by applying a voltage between a cathode and an anode, the working gas is ionized. By supplying the biocompatible material into a plasma frame thus generated, the temperature and airflow of the plasma frame cause the molten biocompatible material to adhere to a metal substrate to form a film of the biocompatible material. In such a plasma spraying method, as the plasma frame becomes closer to the center, it is less susceptible to external factors such as airflow, so that in general, it is considered that a coating material should supplied near a center portion of the frame for high quality film formation.

On the other hand, although an artificial joint in which a metal substrate is coated with HAp are frequently used in joint sites including a hip joint, a load on a HAp film may be large depending on an implant site. When adhesive strength of the HAp film to the metal substrate is low, if a load is applied to the HAp film, peeling may occur, inflammation may occur, and reoperation may be required. Thus, in the artificial joint in which the metal substrate is coated with HAp, the HAp film is required to have high adhesive strength and to be hardly peeled. In the artificial joint in which the metal substrate is coated with HAp, improving the adhesive strength between HAp and the metal substrate by 1 MPa indicates that the adhesive strength per unit area (cm$^2$) is increased by 10 kgf, and it is clear that this is a significant improvement even when considering the area of the artificial joint. Since ceramics such as HAp have low fracture toughness, it is considered that such an improvement in adhesive strength has great technical significance. As a method of increasing the adhesive strength of the HAp film to the metal substrate, it is effective to suitably control conditions (such as type of carrier gas, spray distance, and current value) when HAp is plasma sprayed; however, it is not easy to optimize the plasma spray conditions. In addition, since it is considered that a change in the plasma spray conditions may affect a thermal decomposition property of the HAp film and color tone and lower production efficiency in a production process, it is not practical to significantly change the plasma spray conditions. Thus, from the viewpoint of physical properties of HAp used as a plasma spray material, development of a technique for providing a metal substrate with high adhesive strength is desired.

PRIOR ART DOCUMENT

Patent Document

Patent Document 1: Japanese Patent Laid-open Publication No. H2-140171

SUMMARY OF THE INVENTION

Problems to be Solved by the Invention

An object of the present invention is to provide a plasma spray material capable of forming a HAp film having high adhesive strength to a substrate such as a metal substrate.

Means for Solving the Problem

The present inventors have conducted intensive studies to solve the above-mentioned problems, and found that when a HAp powder having a mode diameter of 550 to 1000 nm at a pore diameter of 5000 nm or less measured by a mercury intrusion method is used as a plasma spray material, a HAp film having high adhesive strength to a substrate such as a metal substrate can be formed. The present invention was completed as a result of further research conducted based on this finding.

In summary, the present invention provides aspects of invention as itemized below.

Item 1. A plasma spray material, including a hydroxyapatite powder having a mode diameter of 550 to 1000 nm at a pore diameter of 5000 nm or less measured by a mercury intrusion method.

Item 2. The plasma spray material according to Item 1, in which the mode diameter is 550 to 750 nm.

Item 3. The plasma spray material according to Item 1 or 2, in which the hydroxyapatite powder has a bulk density of 0.6 g/mL or more.

Item 4. The plasma spray material according to any one of Items 1 to 3, in which the hydroxyapatite powder has a bulk density of 0.7 to 1 g/mL.

Item 5. The plasma spray material according to any one of Items 1 to 4, in which the hydroxyapatite powder has a pore diameter of 5000 nm or more measured by the mercury intrusion method.

Item 6. The plasma spray material according to any one of Items 1 to 5, in which the hydroxyapatite powder has a pore diameter of 20000 to 50000 nm measured by the mercury intrusion method.

Item 7. The plasma spray material according to any one of Items 1 to 6, in which the hydroxyapatite powder has a pore volume of 0.01 to 0.5 cc/g at a pore diameter of 5000 nm or less measured by the mercury intrusion method.

Item 8. The plasma spray material according to any one of Items 1 to 7, in which an average particle diameter (particle diameter at which a cumulative degree is 50%) of the hydroxyapatite powder measured using a laser diffraction/scattering particle size distribution analyzer is more than 30 to 350 μm.

Item 9. The plasma spray material according to any one of Items 1 to 8, in which in a particle size distribution of the hydroxyapatite powder measured using a laser diffraction/scattering particle size distribution analyzer, a particle diameter (D10) at which the cumulative degree is 10% satisfies 45 to 75 µm, a particle diameter (D50) at which the cumulative degree is 50% satisfies 80 to 120 µm, and a particle diameter (D90) at which the cumulative degree is 90% satisfies 130 to 170 µm.

Item 10. The plasma spray material according to any one of Items 1 to 9, which is used for forming a film on a substrate.

Item 11. The plasma spray material according to Item 10, in which the substrate is a metal substrate.

Item 12. The plasma spray material according to Item 11, in which the metal substrate contains a titanium alloy.

Item 13. The plasma spray material according to item 11 or 12, in which the metal substrate is an artificial joint.

Item 14. A method of forming a hydroxyapatite film, comprising plasma-spraying the plasma spray material according to any one of Items 1 to 13 to form a hydroxyapatite film on a substrate.

Item 15. The method of forming a hydroxyapatite film according to Item 14, in which the substrate is a metal substrate.

Item 16. The method of forming a hydroxyapatite film according to Item 15, in which the metal substrate contains a titanium alloy.

Item 17. The method of forming a hydroxyapatite film according to Item 15 or 16, in which the metal substrate is an artificial joint.

Item 18. A use of a hydroxyapatite powder, having a mode diameter of 550 to 1000 nm at a pore diameter of 5000 nm or less measured by a mercury intrusion method, as a plasma spray material.

Advantages of the Invention

The plasma spray material of the present invention can form a HAp film on a substrate with high adhesive strength by plasma spraying, and can suppress peeling of the HAp film even when a load is applied, so that the plasma spray material can be suitably used as a film-forming material of a member required to withstand a load (for example, an implant such as an artificial joint). In addition, the plasma spray material of the present invention can form a HAp film having high whiteness and good appearance on a substrate by plasma spraying.

Although the action mechanism that the plasma spray material of the present invention can form a HAp film on a substrate with high adhesive strength should not be limitedly construed, it can be considered as follows. The HAp powder used in the plasma spray material of the present invention has a specific pore diameter, whereby thermal energy of plasma is easily transmitted uniformly to a particle surface and the inside of the particle, and the entire powder can be uniformly melted. It is considered that particles having a small pore volume have a suitable density, can be easily supplied to a center portion of a plasma frame, and can be supplied uniformly. Thus, it is considered that a moderately melted powder adheres to the substrate to form a strong HAp film.

BRIEF DESCRIPTION OF THE DRAWINGS

FIG. 2 shows microscopic observation images of appearances of HAp powders of Example 4 and Comparative Examples 3 to 8.

EMBODIMENTS OF THE INVENTION

Figure 1:
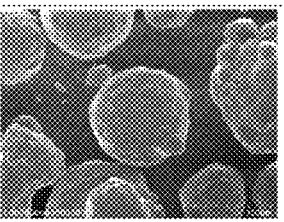
FIG. 1 shows microscopic observation images of appearances of HAp powders of Examples 1 to 3 and Comparative Examples 1 and 2.

The plasma spray material of the present invention is characterized by containing a HAp powder having a mode diameter of 550 to 1000 nm at a pore diameter of 5000 nm or less measured by a mercury intrusion method. Hereinafter, the plasma spray material of the present invention will be described in detail.

[Physical Properties of HAp Powder]

HAp is calcium phosphate represented by the chemical formula $Ca_5(PO_4)_3(OH)$. The HAp powder in the present invention encompasses not only a fine powder form but also a powder form such as granule, granulated material and fine granule.

The HAp powder used in the present invention has a mode diameter (mode pore diameter) of 550 to 1000 nm at a pore diameter of 5000 nm or less measured by a mercury intrusion method. By satisfying such a mode diameter, a HAp film formed by plasma spraying can have high adhesive strength to a substrate. From the viewpoint of further improving the adhesive strength of the HAp film, formed by plasma spraying, to the substrate, the mode diameter at a pore diameter of 5000 nm or less is, for example, preferably 550 to 900 nm, more preferably 550 to 800 nm, and particularly preferably 550 to 750 nm.

In the present invention, the "mode diameter at a pore diameter of 5000 nm or less measured by the mercury intrusion method" is a diameter (mode pore diameter) with the highest appearance ratio in a region with a pore diameter of 5000 nm or less in a pore distribution measured using a mercury porosimeter. In the measurement of the mode diameter, as conditions of the mercury porosimeter under which the pore distribution is measured, a contact angle of mercury is set to 140°, and a surface tension of mercury is set to 480 erg/cm$^2$.

Examples of preferable properties of the HAp powder used in the present invention include having a pore diameter of 5000 nm or more measured by the mercury intrusion method, preferably having a pore diameter of 20000 to 50000 nm measured by the mercury intrusion method. In the present invention, "having a pore diameter of 5000 am or more measured by the mercury intrusion method" means that in the pore distribution measured using a mercury porosimeter, the pore diameter is found to be in the range of 5000 nm or more. Moreover, "having a pore diameter of 20000 to 50000 nm measured by the mercury intrusion method" means that in the pore distribution measured using a mercury porosimeter, the pore diameter is found to be in the range of 20000 to 50000 nm. The conditions of the mercury porosimeter under which the pore distribution is measured are the same as those in the case of the above-mentioned "mode diameter at a pore diameter of 5000 nm or less".

In the HAp powder used in the present invention, the mode diameter at a pore diameter of 5000 inn or more measured by the mercury intrusion method is not particularly limited, but may be, for example, 5000 to 300000 nm, preferably 10000 to 100000 nm, more preferably 20000 to 50000 nm, and particularly preferably 35000 to 45000 nm.

In the present invention, the "mode diameter at a pore diameter of 5000 nm or more measured by the mercury intrusion method" is a diameter (mode pore diameter) with the highest appearance ratio in a region with a pore diameter of 5000 nm or more in a pore distribution measured using a mercury porosimeter. In the measurement of the mode diameter, the conditions of the mercury porosimeter under which the pore distribution is measured are the same as those in the case of the above-mentioned "mode diameter at a pore diameter of 5000 nm or less".

In the HAp powder used in the present invention, a pore volume is not particularly limited, but the pore volume at a pore diameter of 5000 nm or less measured by the mercury intrusion method is preferably 0.01 to 0.5 cc/g, more preferably 0.01 to 0.4 cc/g, still more preferably 0.05 to 0.35 cc/g, and particularly preferably 0.1 to 0.35 cc/g. By satisfying such a pore volume, the adhesive strength of the HAp film, formed by plasma spraying, to the substrate can be further improved.

In the present invention, the "pore volume at a pore diameter of 5000 nm or less measured by the mercury intrusion method" is a cumulative pore volume in a region with a pore diameter of 5000 nm or less in a pore volume measured using a mercury porosimeter. In the measurement of the pore volume, the conditions of the mercury porosimeter under which the pore volume is measured are the same as those in the case of the above-mentioned "mode diameter at a pore diameter of 5000 nm or less".

In the HAp powder used in the present invention, the pore volume at a pore diameter of 5000 nm or more measured by the mercury intrusion method is not particularly limited, but is, for example, 0.01 to 1 cc/g, preferably 0.01 to 0.8 cc/g, and more preferably 0.3 to 0.6 cc/g.

In the present invention, the "pore volume at a pore diameter of 5000 nm or more measured by the mercury intrusion method" is a cumulative pore volume in a region with a pore diameter of 5000 nm or more in a pore volume distribution measured using a mercury porosimeter. In the measurement of the pore volume, the conditions of the mercury porosimeter under which the pore volume distribution is measured are the same as those in the case of the above-mentioned "mode diameter at a pore diameter of 5000 nm or less".

A bulk density of the HAp powder used in the present invention is not particularly limited, but is, for example, 0.6 g/mL or more, preferably 0.7 g/mL or more, more preferably 0.7 to 3 g/mL, still more preferably 0.3 to 1.3 g/mL, and particularly preferably 0.7 to 1 g/mL. By satisfying such a bulk density, the adhesive strength of the HAp film, formed by plasma spraying, to the substrate can be further improved.

In the present invention, the "bulk density" is a value calculated according to the following formula by weighing 10.0 g of the HAp powder, gently placing the HAp powder in a 50 mL graduated cylinder, carefully leveling an upper surface of the HAp powder without being compressed, and measuring a powder volume (loose bulk volume).

Bulk density (g/mL)=powder weight (g)/powder volume (mL)

A tap density of the HAp powder used in the present invention is not particularly limited, but is, for example, 0.8 g/mL or more, preferably 0.8 to 3 g/mL, and more preferably 0.9 to 1.5 g/mL.

In the present invention, the "tap density" is a value calculated according to the following formula by weighing 10.0 g of the HAp powder, placing the HAp powder in a 50 mL graduated cylinder, performing tapping at a height of 4 cm at a speed of 100/250 seconds using a tapping device, and measuring a powder volume (tap volume).

Tap density (g/mL)=powder weight (g)/powder volume (mL)

An average particle diameter of the HAp powder used in the present invention is not particularly limited, but may be, for example, more than 30 to 350 μm, preferably 50 to 150 μm, more preferably 70 to 120 μm, and particularly preferably 80 to 110 μm. By satisfying such an average particle diameter, the adhesive strength of the HAp film, formed by plasma spraying, to the substrate can be further improved.

In the present invention, the "average particle diameter" is a particle diameter (D50, median diameter) at which a cumulative degree is 50%, which is measured using a laser diffraction/scattering particle size distribution analyzer.

The particle size distribution of the HAp powder used in the present invention is not particularly limited, but a particle diameter (D90) at which the cumulative degree is 90% may be, for example, 2000 μm or less, preferably more than 30 to 2000 μm, more preferably more than 30 to 200 μm, still more preferably 100 to 200 μm, and particularly preferably 140 to 155 μm. Especially, preferred is a HAp powder having a particle size distribution in which a particle diameter (D10) at which the cumulative degree is 10% is 45 to 75 μm, the particle diameter (D50) at which the cumulative degree is 50% is 80 to 120 μm, and the particle diameter (D90) at which the cumulative degree is 90% is 130 to 170 μm. Further especially, most preferred is a HAp powder having a particle size distribution in which the particle diameter (D10) at which the cumulative degree is 10% is 50 to 65 μm, the particle diameter (D50) at which the cumulative degree is 50% is 85 to 110 μm, and the particle diameter (D90) at which the cumulative degree is 90% is 140 to 155 μm. By satisfying such a particle size distribution, the adhesive strength of the HAp film, formed by plasma spraying, to the substrate can be further improved.

In the present invention, D10, D50 and D90 are values measured using a laser diffraction/scattering particle size distribution analyzer.

A BET specific surface area of the HAp powder used in the present invention is not particularly limited, but may be, for example, 10 m$^2$/g or less, preferably 0.1 to 10 m$^2$/g, more preferably 0.1 to 5 m$^2$, and particularly preferably 0.1 to 3 m$^2$/g.

In the present invention, the BET specific surface area is a value measured by the following method using a high-speed specific surface area pore distribution measuring device. First, 1.0 g of the HAp powder is accurately weighed, sealed in an adsorption pipe, and degassed at 105° C. for 3 hours. Next, an adsorption isotherm of nitrogen gas at the liquid nitrogen gas temperature is worked out, and a specific surface area (m²/g) is calculated in accordance with a multipoint BET method, using the adsorption isotherm.

In the HAp powder used in the present invention, the pore volume measured by a gas adsorption method is not particularly limited, but may be, for example, 0.001 to 1.4 cc/g, preferably 0.001 to 0.05 cc/g, and more preferably 0.001 to 0.01 cc/g.

In the present invention, the pore volume measured by the gas adsorption method is a value measured by the following method using a high-speed specific surface area pore distribution measuring device. First, 1.0 g of the HAp powder is accurately weighed, sealed in an adsorption pipe, and degassed at 105° C. for 3 hours. Next, an adsorption isotherm of nitrogen gas at the liquid nitrogen gas temperature is worked out, and a total pore volume (cc/g) was calculated from a gas adsorption amount at a liquid relative pressure $P/P_0$ ($P_0$: saturated vapor pressure) of 0.995.

In the present invention, the average pore diameter measured by the gas adsorption method is not particularly limited, but may be, for example, 1 to 20 nm, preferably 5 to 15 nm, and more preferably 8 to 12 nm.

In the present invention, the "average pore diameter measured by the gas adsorption method" is a value calculated according to the following formula:

average pore diameter (nm)=$4V/S\times 1000$

V: pore volume (cc/g) measured by gas adsorption method
S: specific surface area (m²/g)

[Method of Producing HAp Powder]

A method of producing the HAp powder used in the present invention is not particularly limited as long as the HAp powder having the above-mentioned physical properties is obtained; however, preferred examples of the method of producing the HAp powder having the above-mentioned physical properties include a production method including the following first step and second step.

First step: the HAp powder is obtained by (1) a wet method including a sequential addition step of adding dropwise phosphoric acid to a suspension in which calcium hydroxide is suspended, or (2) a wet method including a sequential addition step of adding a suspension in which calcium hydroxide is suspended to a phosphoric acid aqueous solution in which phosphoric acid is dissolved in water.

Second step: the HAp powder obtained in the first step is subjected to a burning treatment at a temperature of more than 1050° C. to less than 1400° C.

In the first step, (1) phosphoric acid is added dropwise to the suspension in which calcium hydroxide is suspended, or (2) the suspension in which calcium hydroxide is suspended is added to the phosphoric acid aqueous solution in which phosphoric acid is dissolved in water, whereby calcium ions and phosphate ions may be reacted to carry out a HAp synthesis reaction [$10Ca(OH)_2+6H_3PO_4 \rightarrow Ca_{10}(PO_4)_6(OH)_2$]. In the first step, the ratio of calcium hydroxide and phosphoric acid finally coexisting may be adjusted so as to be equal to the ratio of calcium and phosphorus of HAp. A liquid in which calcium hydroxide is suspended as an emulsion state in water can be obtained by adding calcium oxide to water and causing a hydration reaction. When phosphoric acid is added dropwise to the suspension in which calcium hydroxide is suspended, the phosphoric acid to be added dropwise is preferably in the form of the phosphoric acid aqueous solution in which phosphoric acid is dissolved in water. When phosphoric acid is adding dropwise to the suspension in which calcium hydroxide is suspended, a rate at which phosphoric acid is added dropwise may be appropriately adjusted so that pH of a reaction liquid after the dropwise addition is 9 or less, and, for example, phosphorus (P) atoms may be in a range of 0.05 to 0.6 mol/h, preferably 0.1 to 0.3 mol/h, and more preferably 0.2 mol/h per 1 mol of calcium (Ca) atoms. If the suspension in which calcium hydroxide is suspended is added to the phosphoric acid aqueous solution in which phosphoric acid is dissolved in water, calcium (Ca) atoms may be in a range of 0.05 to 0.6 moL/h per 1 mol of phosphorus (P) atoms. When HAp is synthesized by a wet method in which the suspension of calcium hydroxide and phosphoric acid are simultaneously mixed, the above-mentioned physical properties cannot be provided, and HAp that can be plasma sprayed cannot be formed.

From the viewpoint of efficiently producing the HAp powder used in the present invention, the first step is preferably performed by the wet method including the sequential addition step of adding dropwise phosphoric acid to the suspension in which calcium hydroxide is suspended.

The HAp produced in the first step is dried by spray drying, a box-shaped dryer, a band dryer, a vacuum dryer, a freeze dryer, a microwave dryer, a drum dryer, a fluid dryer, or the like and then may be subjected to the second step (burning treatment). As long as the HAp powder having the above-mentioned physical properties can be obtained, the HAp powder obtained in the first step may be subjected to treatment such as wet granulation, dry granulation, or grinding for the purpose of adjusting the particle diameter, if necessary, prior to the second step.

The HAp powder produced in the first step is subjected to burning treatment under a temperature condition of more than 1050° C. to less than 1400° C. in the second step. Conventionally, the burning treatment of the HAp powder produced by a wet method is generally performed under a temperature condition of 1000° C. or lower; however, under such a temperature condition, a HAp powder having the above-mentioned physical properties cannot be obtained. In the present invention, in the second step, by setting the temperature condition of the burning treatment of the HAp powder produced in the first step to a temperature of more than 1050° C. to less than 1400° C., the HAp powder having the above-mentioned physical properties can be obtained. The temperature condition of the burning treatment in the second step is preferably more than 1050 to 1300° C., and more preferably 1100 to 1200° C.

A holding time of the temperature condition of the burning treatment may be appropriately set within a range in which the HAp powder having the above-mentioned physical properties is generated in consideration of the temperature condition. Although it suffices that the holding time has reached the above-mentioned temperature condition of the burning treatment even for only a moment, the holding time is preferably 0.1 to 10 hours, and more preferably 1 to 5 hours.

By performing the second step in this way, a HAp powder (HAp powder used in the present invention) having the above-mentioned physical properties can be obtained. The HAp powder obtained in the second step is desirably sized using a sieve. The mesh size of the sieve to be used is not particularly limited, but may be, for example, 30 μm or more, preferably 50 to 500 μm, and more preferably 150 to 300 μm.

[Use and Usage]

In the present invention, the HAp powder is used as a plasma spray material. The "plasma spray material" is a powder (powder as a raw material of a film to be formed) to be plasma sprayed. The "plasma spraying" is a technique of heating a plasma spray material (powder) by plasma, melting the material to form liquid fine particles, and colliding the liquid fine particles against a substrate surface at high speed together with a plasma jet to form a film of the plasma spray material on the substrate.

In the plasma spraying using the plasma spray material of the present invention, a material of a substrate on which a HAp film is to be formed is not particularly limited, but examples include metals such as titanium alloys (Ti-6Al-4V alloy, Ni—Ti, etc.), cobalt alloys (Co—Cr—Ni alloy, Co—Cr—Mo, Co—Cr—W—Ni, etc.), magnesium alloys (Mg—Y—RE, Mg—Ca—Zn, Mg—Li—Al, etc.), stainless steel (SUS316L, SUS304, etc.), titanium, cobalt, molybdenum, niobium, tantalum, gold, platinum, tungsten, iridium, and inconel; ceramics such as alumina and zirconia; and polymeric materials such as polyethylene, polyester, polypropylene, polyamide, polyether, polyether ketone, polyether ether ketone, acrylic, polystyrene, polytetrafluoroethylene, hydroxyethyl methacrylate, polyamide, polylactic acid, polyglycolic acid, polylactide, polyglycolide, polyparadioxanone, trimethylene carbonate, and ε-caprolactone. Among these, metal is preferable, and titanium alloy is more preferable.

The type (use) of the substrate on which the HAp film is to be formed is not particularly limited, and examples include implants such as artificial joints, artificial roots, and artificial bones; and housings of in-vivo indwelling devices such as auxiliary artificial hearts, artificial blood vessels, stents, pacemakers, sutures, catheters, artificial skins, artificial muscles, and intraocular lenses. Among these, implants (particularly, artificial joints) are likely to be loaded in a living body and are strongly required to have properties that a HAp film provided on a substrate is firmly adhered and hardly peeled off. Since the plasma spray material of the present invention can form a HAp film that can satisfy the above properties required for implants (particularly, artificial joints), this plasma spray material is suitably used as a material used for forming a HAp film provided on a surface of the implant (particularly, artificial joint).

Conditions of plasma spraying under which a HAp film is formed on a substrate using the plasma spray material of the present invention are not particularly limited, and may be appropriately set within a range of usually employed conditions of plasma spraying depending on the type of the substrate, thickness of the HAp film to be formed, and the like.

EXAMPLES

Hereinafter, the present invention will be described specifically with reference to Examples. The present invention is not limited to the examples.
1. Production and Physical Property Evaluation of HAp Powder
1-1. Production of HAp Powder Example 1

After 6 L of water and 1 kg of calcium oxide were charged into a reaction tank to cause a hydration reaction, water was added to a suspension to adjust the total to 15 L. Next, the mixture was heated to 50° C., and a phosphoric acid aqueous solution was added at a dropping rate at which phosphorus (P) atoms are in a range of 0.2 mol/h per 1 mol of calcium (Ca) atoms until pH reached 8. The obtained solution was heated to 95° C. or higher and reacted for 2 hours.

Next, the obtained reaction solution was spray-dried using a spray dryer equipped with a disk type spraying means, and a dried product was collected.

In addition, the obtained dried product was burned at 1100° C. for 3 hours (heating rate 65° C./h) using an electric furnace (manufactured by Kusaba Chemical Co., Ltd.). After cooling, a HAp powder was obtained.

Example 2

A HAp powder was obtained under the same conditions as in Example 1 except that the burning temperature was changed to 1150° C.

Example 3

A HAp powder was obtained under the same conditions as in Example 1 except that the burning temperature was changed to 1200° C.

Example 4

A HAp powder was obtained under the same conditions as in Example 1 except that the burning temperature was changed to 1250° C.

Comparative Example 1

A HAp powder was obtained under the same conditions as in Example 1 except that the burning temperature was changed to 800° C.

Comparative Example 2

A HAp powder was obtained under the same conditions as in Example 1 except that the burning temperature was changed to 1000° C.

Comparative Example 3

A HAp powder was obtained under the same conditions as in Example 1 except that the burning temperature was changed to 1050° C.

Comparative Example 4

A HAp powder was obtained under the same conditions as in Example 1 except that the burning temperature was changed to 1400° C.

Comparative Example 5

2.5 L of a suspension containing 25% by weight of calcium hydroxide and 1 L of a solution containing 50% by weight of phosphoric acid were simultaneously added dropwise to 5 L of water at pH 7 over 3 hours.

Next, the obtained reaction solution was spray-dried using a spray dryer equipped with a disk type spraying means, and a dried product was collected.

In addition, the obtained dried product was burned at 1200° C. for 3 hours (heating rate 65° C./h) using an electric furnace (manufactured by Kusaba Chemical Co., Ltd.). After cooling, a HAp powder was obtained.

Comparative Example 6

A HAp powder was obtained under the same conditions as in Comparative Example 5 except that the burning temperature was changed to 1000° C.

Comparative Example 7

After 6 L of water and 1 kg of calcium oxide were charged into a reaction tank to cause a hydration reaction, water was added to a suspension to adjust the total to 15 L. Next, the mixture was heated to 50° C., and a phosphoric acid aqueous solution was added until the pH reached 8. The obtained solution was heated to 95° C. or higher and reacted for 2 hours.

Next, the obtained reaction liquid was wet-pulverized, and the obtained slurry was then granulated and dried using a fluidized bed granulator to collect a dried product.

In addition, the obtained dried product was burned at 800° C. for 3 hours (heating rate 65° C./h) using an electric furnace (manufactured by Kusaba Chemical Co., Ltd.). After cooling, a HAp powder was obtained.

Comparative Example 8

A commercially available HAp powder (Hydroxyapatite (Medipure 20-15No101) manufactured by Medicoat AG) was used.

1-2. Method of Evaluating Physical Properties of HAp Powder

For each obtained HAp powder, in the following manner, bulk density, tap density, average particle diameter and particle size distribution, mode diameter and pore volume at a pore diameter of 5000 nm or less/5000 nm or more (mercury intrusion method), BET specific surface area, average pore diameter (gas adsorption method), pore volume (gas adsorption method), appearance, and diffraction peak in powder X-ray diffraction analysis were measured.

[Bulk Density]

10.0 g of the HAp powder was weighed and gently placed in a 50 mL graduated cylinder, an upper surface of the HAp powder was carefully leveled without being compressed, the powder volume (loose bulk volume) was measured, and the bulk density was calculated by the following formula:

Bulk density (g/mL)=powder weight (g)/powder volume (mL)

[Tap Density]

10.0 g of the HAp powder was weighed and placed in a 50 mL graduated cylinder, tapping was performed at a height of 4 cm at a speed of 100/250 seconds using a tapping device, the powder volume (tap volume) was measured, and the tap density was calculated by the following formula:

Tap density (g/mL)=powder weight (g)/powder volume (mL)

[Average Particle Diameter and Particle Size Distribution]

Hydroxyapatite particles were dispersed in water, the particle size distribution was measured using a laser diffraction/scattering particle size distribution analyzer ("MICROTRAC MT3300EXII" manufactured by MicrotracBEL Corp.), and D10, D50 (average particle diameter), and D90 were obtained.

[Mode Diameter and Pore Volume at Pore Diameter of 5000 nm or less/5000 nm or More (Mercury Intrusion Method)]

Using a mercury porosimeter ("poremaster60GT" manufactured by Quantachrome Corporation), the mode diameter and the pore volume were measured under the following conditions. 0.1 to 0.2 g of hydroxyapatite particles were sealed in a measurement cell, and the mode diameter and the pore volume were calculated from the measured pressure, with a mercury contact angle of 140° and a mercury surface tension of 480 erg/cm$^2$. The analysis range was divided into a range of a pore diameter of 5000 nm or less and a range of a pore diameter of 5000 nm or more.

[BET Specific Surface Area]

Using a high-speed specific surface area pore distribution measuring device ("NOVA-4000" manufactured by Quantachrome Corporation), the BET specific surface area was measured under the following operating conditions.

Pretreatment: 1.0 g of a sample was accurately weighed, sealed in an adsorption pipe, and degassed at 105° C. for 3 hours.

Measurement and analysis: an adsorption isotherm of nitrogen gas at the liquid nitrogen gas temperature was worked out, and the specific surface area (m$^2$/g) was calculated in accordance with a multipoint BET method, using the adsorption isotherm.

[Pore Volume (Gas Adsorption Method)]

Using a high-speed specific surface area pore distribution measuring device ("NOVA-4000" manufactured by Quantachrome Corporation), the pore volume was measured by the gas adsorption method under the following operating conditions.

Pretreatment: 1.0 g of a sample was accurately weighed, sealed in an adsorption pipe, and degassed at 105° C. for 3 hours.

Measurement and analysis: an adsorption isotherm of nitrogen gas at the liquid nitrogen gas temperature was worked out, and a total pore volume (cc/g) was calculated from a gas adsorption amount at a relative pressure $P/P_0$ ($P_0$: saturated vapor pressure) of 0.995.

[Average Pore Diameter (Gas Adsorption Method)]

The average pore diameter (gas adsorption method) was calculated by the following formula:

average pore diameter (nm)=4$V$/$S$×1000

V: pore volume (gas adsorption method) (cc/g)
S: BET specific surface area (m$^2$/g)

[Appearance]

Using a field emission scanning electron microscope, the appearance of each HAp powder was observed at 500 and 10000 times magnification.

[Powder X-Ray Diffraction Analysis]

Using an X-ray diffractometer "SmartLab" (manufacturer: Rigaku Corporation), measurement was performed in a range of 2θ=20 to 50° (measurement conditions: target: Cu, tube voltage: 40 kV, tube current: 30 mA, scan range: 20 to 50°, scanning speed: 40.000°/min, scan step: 0.02°, scan mode: continuous). The measurement results were analyzed using Rigaku Data Analysis Software PDXL version 2.1.3.6 to qualify each peak.

2. Formation of HAp Film on Metal Substrate Surface and Evaluation of Physical Properties 2-1. Formation of HAp Film on Metal Substrate Surface After a surface of a metal substrate made of a Ti-6Al-4V alloy in the form of a pellet with φ25 and thickness of 6 mm was roughened by blasting, a film was obtained using each HAp powder under the following plasma spray conditions under atmospheric pressure.

[Table 1]
Plasma Spray Condition

| Item | | Condition |
|---|---|---|
| Device | | MF-P-HVOF-K1000 manufactured by GTV |
| Working gas Ar | SLPM | 40 |
| $H_2$ | SLPM | 3 |
| Carrier gas | SLPM | 3.5 |
| Current value | A | 600 |
| Spray distance | mm | 100 |

2-2. Evaluation of Physical Properties of HAp Film

For the HAp film formed on the metal substrate, the adhesive strength, cross-sectional hardness, thickness, surface roughness, cross-sectional appearance, and color difference were measured by the following method, and, in addition, a film forming speed during HAp film formation was determined. The measurement of the color difference was performed only on the HAp film formed with the HAp of Examples 1 to 3.

[Adhesive Strength of HAp Film]

Based on a test method defined in ISO13779-4 (2002), the adhesive strength between the HAp film and the metal substrate was measured.

[Cross-Sectional Hardness of HAp Film]

The cross-sectional hardness of the HAp film at a test force of 0.3 kg was measured using a Vickers hardness tester.

[Thickness of HAp Film]

The thickness of the HAp film was measured using a micrometer.

[Surface Roughness of HAp Film]

Using a surface roughness meter, the surface roughness of a hydroxyapatite film was measured based on JIS B 0031 (1994).

[Cross-Sectional Appearance]

Using a scanning electron microscope, a cross section of the HAp film was observed at 500 and 1000 times magnification.

[Film Forming Speed During HAp Film Formation]

From the thickness of the HAp film and the number of passes, the film forming speed during HAp film formation was calculated according to the following formula:

film forming speed (μm/pass)=HAp film thickness (μm)/number of passes (pass)

[Color Difference]

For a HAp film formed on a metal substrate, using a differential colorimeter "ZE6000" manufactured by Nippon Denshoku Industries Co., Ltd., under reflection conditions, L value, a value, and b value were calculated, and W (whiteness) was calculated from these values by the following formula:

$$W=100-[(100-L)^2+(a^2+b^2)]^{1/2}$$

3. Evaluation Results

Figure 3:
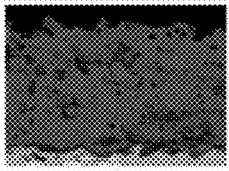
FIG. 3 shows microscopic observation images of cross-sectional appearances of HAp films formed by plasma spraying the HAp powders of Examples 1 to 3 and Comparative Examples 1 and 2.
Figure 4:
FIG. 4 shows microscopic observation images of cross-sectional appearances of HAp films foil led by plasma spraying the HAp powders of Comparative Examples 3, 7 and 8.
Figure 4:
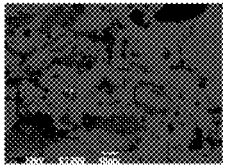
Figure 4:
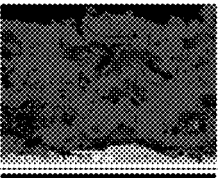
Figure 4:
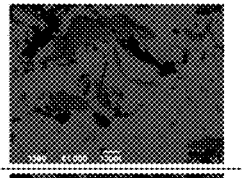
Figure 4:
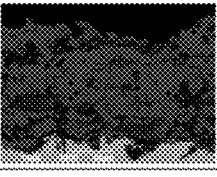
Figure 4:
Figure 5:
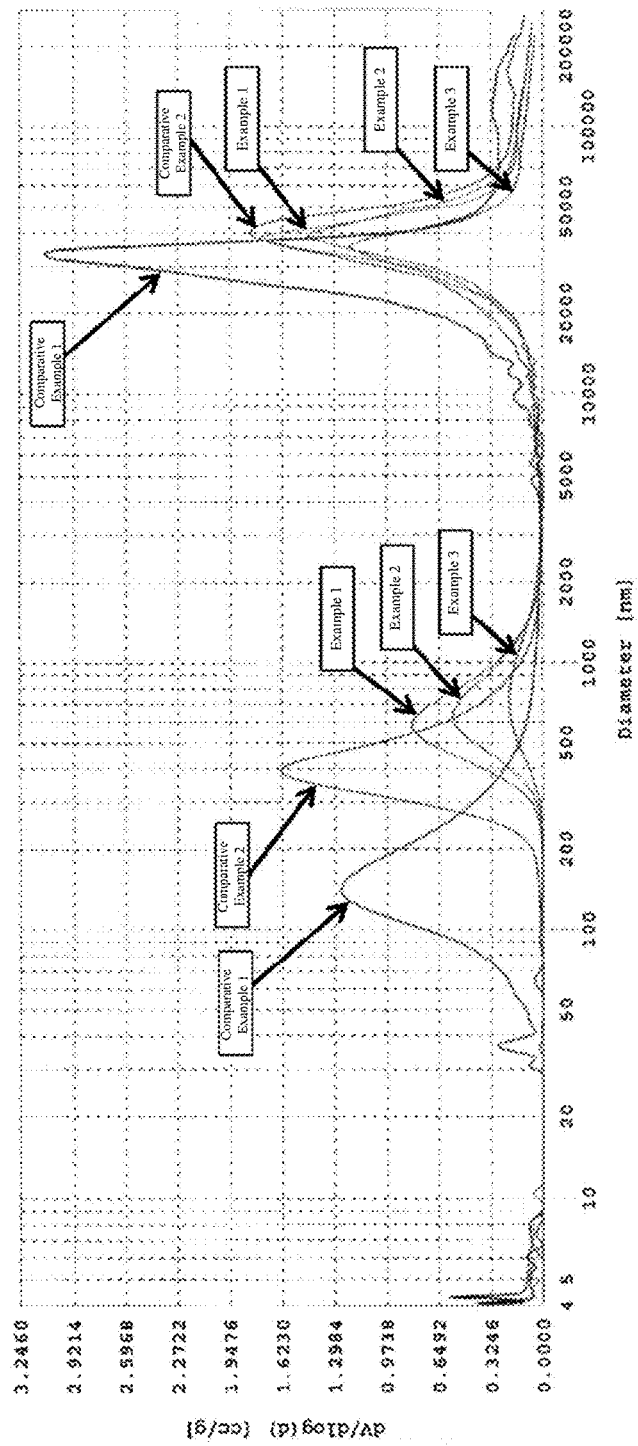
FIG. 5 shows results of obtaining pore diameter distributions of the HAp powders of Examples 1 to 3 and Comparative Examples 1 and 2 by a mercury intrusion method.
Figure 6:
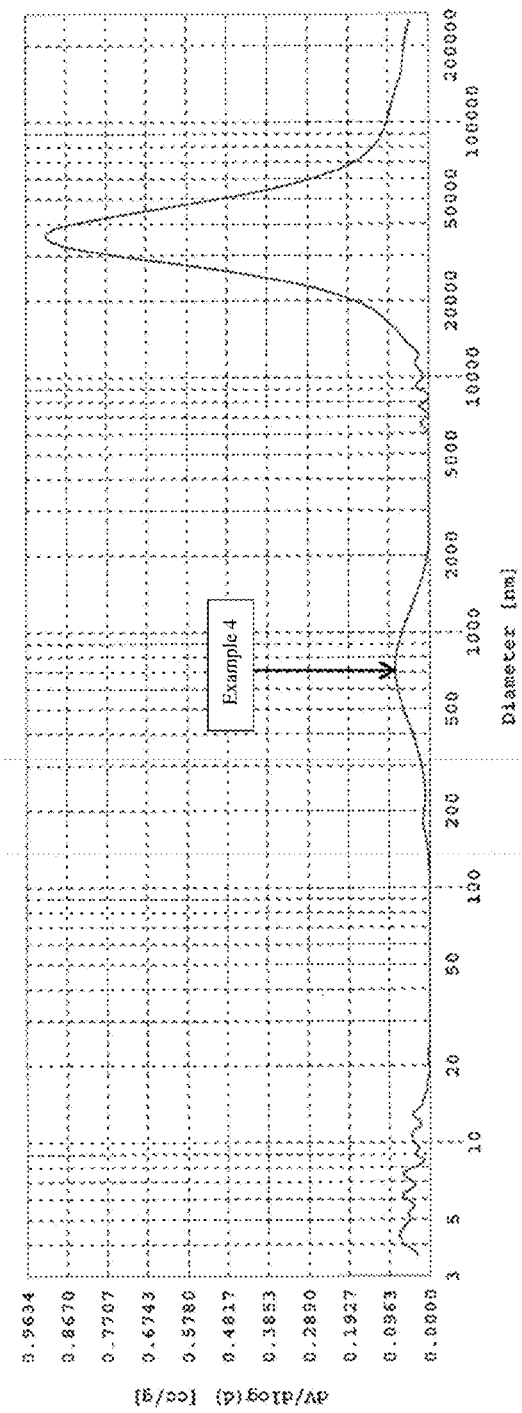
FIG. 6 shows a result of obtaining the pore diameter distribution of the HAp powder of Example 4 by the mercury intrusion method.
Figure 7:
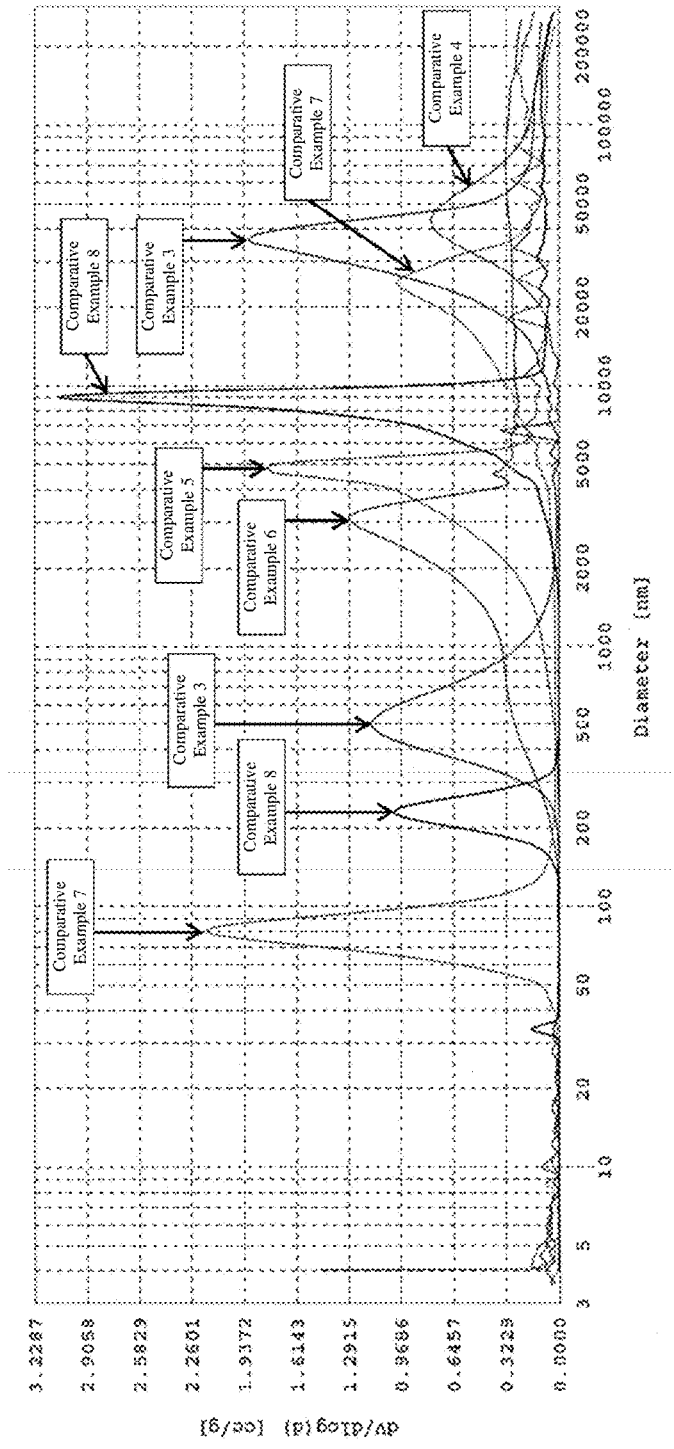
FIG. 7 shows results of obtaining the pore diameter distributions of the HAp powders of Comparative Examples 3 to 8 by the mercury intrusion method.
Figure 8:
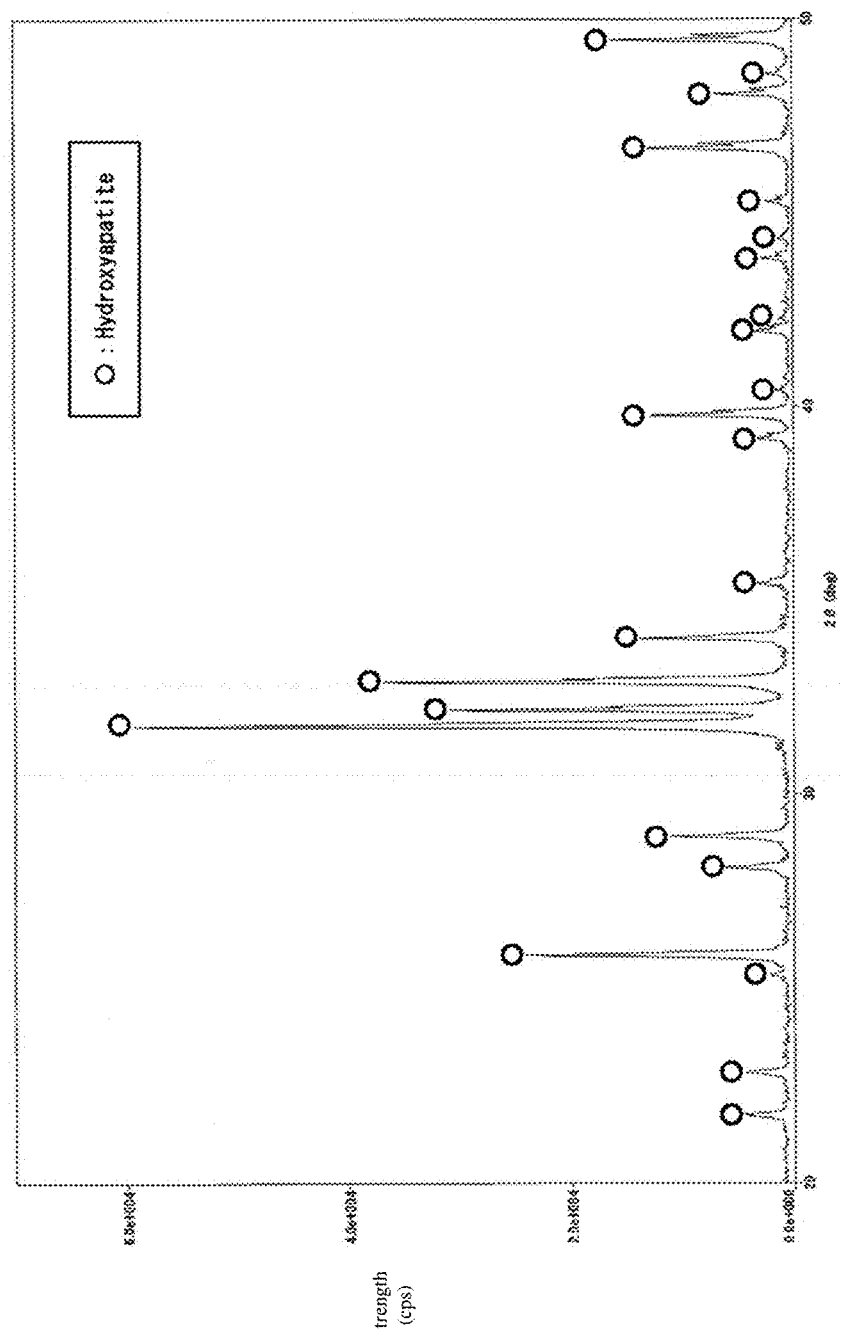
FIG. 8 shows a result of a powder X-ray diffraction analysis of Example 2.
Figure 9:
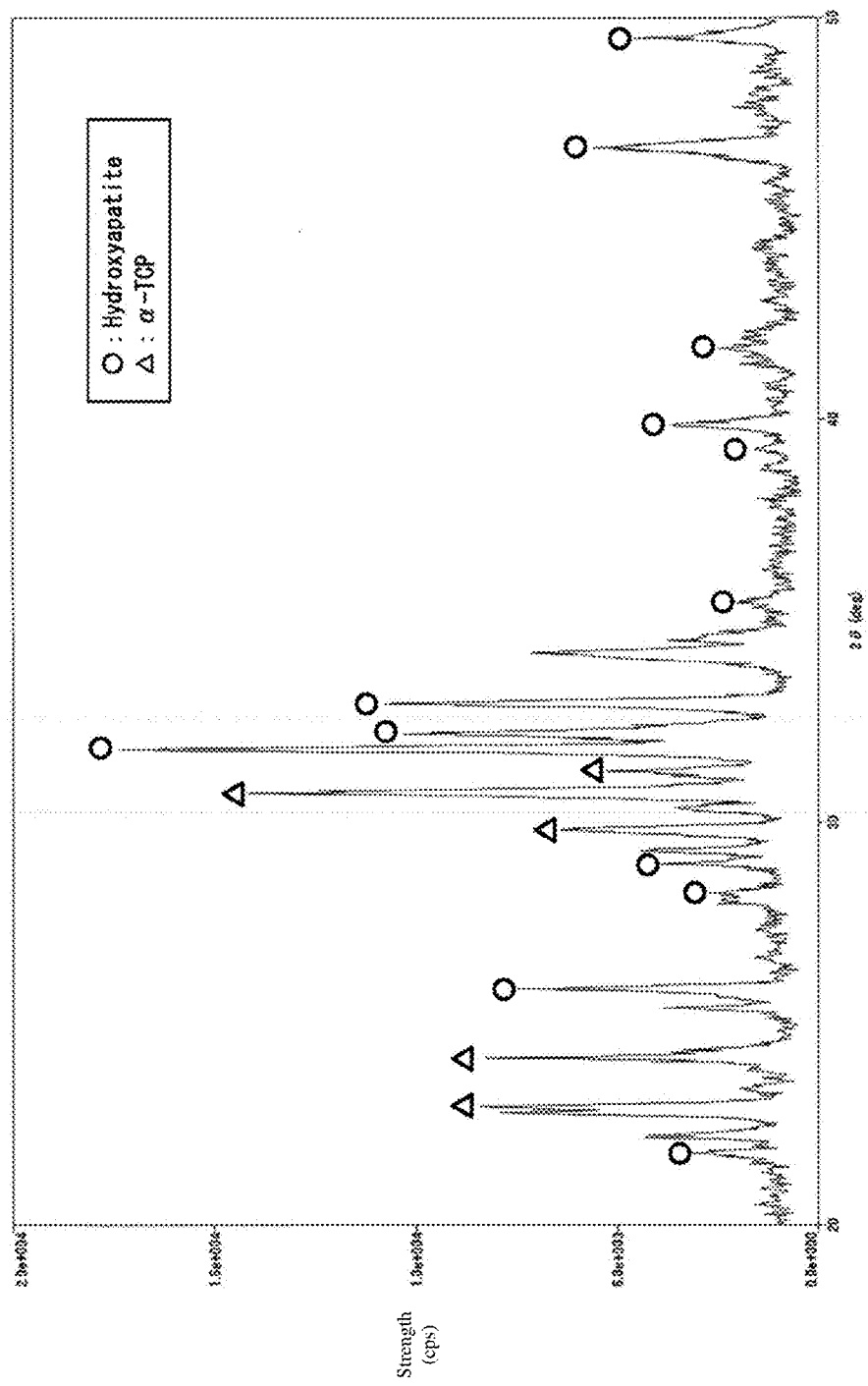
FIG. 9 shows a result of the powder X-ray diffraction analysis of Comparative Example 4.

The results are shown in Tables 2 and 3, and FIGS. 1 to 9. FIGS. 1 and 2 show microscopic observation images of the appearances of the HAp powders. FIGS. 3 and 4 show microscopic observation images of the cross-sectional appearances of the HAp films. FIGS. 5 to 7 show results of measurement of pore diameter distributions of the HAp powders by the mercury intrusion method. FIG. 8 shows a result of a powder X-ray diffraction analysis of the HAp powder of Example 2. FIG. 9 shows a result of the powder X-ray diffraction analysis of the HAp powder of Comparative Example 4.

The HAp film formed using the HAp powders of Examples 1 to 3 had higher adhesive strength and cross-sectional hardness than those of Comparative Examples 1, 2 and 3, and from the image of the cross-sectional appearance of the film shown in FIG. 3, it was confirmed that the number of unmelted particles was small. In particular, with respect to the adhesive strength, the adhesive strength of Examples 1 to 3 is improved by 5.9 to 7.3 MPa compared with Comparative Examples 1 and 2, and improved by 6.7 to 8.0 MPa compared with Comparative Example 3, which indicates that the adhesive strength is improved by 59 to 73 kgf per unit area (cm$^2$). Due to the dramatically improvement of the load resistance, it is considered that the HAp film can be applied to a portion to which a large load is applied. In addition, this adhesive strength exceeded 15 MPa which was a recommended value of the adhesive strength in ISO 13779. This is considered to be due to the fact that the HAp powder supplied to a plasma spraying device is supplied to a center portion of a plasma frame at a high rate, and the entire HAp powder is uniformly melted, so that a film having high strength is formed without remaining of an unmelted powder on a film. It was confirmed that the HAp film formed using the HAp powders of Examples 1 to 3 had high whiteness and little deterioration in color tone. This is considered to be due to the absence of thermal decomposition.

When the HAp powders of Examples 1 to 3 were used, the film forming speed during HAp film formation was high. This is considered to be due to the fact that the HAp powders of Examples 1 to 3 were easily supplied to the center portion of the plasma frame, and were used for spray film formation at a high rate. On the other hand, the HAp powders of Comparative Examples 5 and 6 could not be plasma sprayed. This is considered to be due to the fact that each HAp powder cannot be supplied to the center portion of the plasma frame. In Comparative Example 4, as shown in FIG. 9, hydroxyapatite is decomposed, and related substances such as α-TCP other than hydroxyapatite are mixed; therefore, Comparative Example 4 is not suitable as a plasma spray material used for living tissue where strength is required.

TABLE 2

| Test item | Example 1 | Example 2 | Example 3 | Example 4 |
|---|---|---|---|---|
| Bulk density (g/mL) | 0.71 | 0.83 | 0.95 | 1.22 |
| Tap density (g/mL) | 0.91 | 1.05 | 1.25 | 1.48 |
| Average particle diameter (D50) (μm) | 95.7 | 93.7 | 89.4 | 86.1 |
| Particle size distribution | | | | |
| D10 (μm) | 60.1 | 56.3 | 54.1 | 55.5 |
| D50 (μm) | 95.7 | 93.7 | 89.4 | 86.1 |
| D90 (μm) | 151.0 | 152.9 | 145.4 | 137.9 |
| Mode diameter at pore diameter of 5000 nm or less (mercury intrusion method) (nm) | 577 | 620 | 726 | 740 |

TABLE 2-continued

| Test item | Example 1 | Example 2 | Example 3 | Example 4 |
|---|---|---|---|---|
| Mode diameter at pore diameter of 5000 nm or more (mercury intrusion method) (nm) | 37970 | 39320 | 35560 | 35390 |
| Pore volume at pore diameter of 5000 nm or less (mercury intrusion method) (cc/g) | 0.32 | 0.25 | 0.12 | 0.06 |
| Pore volume at pore diameter of 5000 nm or more (mercury intrusion method) (cc/g) | 0.52 | 0.49 | 0.39 | 0.36 |
| BET specific surface area (m$^2$/g) | 2.6 | 1.9 | 2.0 | 1.0 |
| Average pore diameter (gas adsorption method) (nm) | 10.2 | 11.3 | 8.3 | 8.0 |
| Pore volume (gas adsorption method) (cc/g) | 0.007 | 0.005 | 0.004 | 0.002 |
| Spray test result | | | | |
| Adhesive strength (MPa) | 17.9 | 18.5 | 19.2 | Unmeasured |
| Cross-sectional hardness (HV0.3) | 152 | 153 | 171 | Unmeasured |
| Film thickness (μm) | 150 | 160 | 150 | Unmeasured |
| Surface roughness (Ra, μm) | 7.6 | 7.5 | 8.0 | Unmeasured |
| Film forming speed (μm/pass) | 25 | 27 | 30 | Unmeasured |
| Color difference | | | | |
| L | 87.9 | 85.2 | 82.0 | Unmeasured |
| a | −0.4 | −0.1 | −0.3 | Unmeasured |
| b | 3.1 | 5.0 | 4.8 | Unmeasured |
| W | 84.4 | 80.9 | 77.1 | Unmeasured |

TABLE 3

| Test item | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|
| Bulk density (g/mL) | 0.44 | 0.57 | 0.65 | 1.43 | 0.63 | 0.44 | 0.67 | 0.48 |
| Tap density (g/mL) | 0.54 | 0.71 | 0.80 | 1.49 | 1.19 | 0.83 | 0.87 | 0.63 |
| Average particle diameter (D50) (μm) | 91.8 | 101.3 | 101.0 | 92.3 | 13.0 | 13.6 | 100.9 | 101.2 |
| Particle size distribution | | | | | | | | |
| D10 (μm) | 57.5 | 58.1 | 61.0 | 58.6 | 6.1 | 6.1 | 30.1 | 64.7 |
| D50 (μm) | 91.8 | 101.3 | 101.0 | 92.3 | 13.0 | 13.6 | 100.9 | 101.2 |
| D90 (μm) | 147.7 | 167.3 | 164.6 | 147.1 | 36.2 | 32.4 | 205.3 | 156.1 |
| Mode diameter at pore diameter of 5000 nm or less (mercury intrusion method) (nm) | 140 | 391 | 505 | 5 | 4823 | 3090 | 81 | 231 |
| Mode diameter at pore diamater of 5000 nm or more (mercury intrusion method) (μm) | 33390 | 40570 | 36500 | 43520 | 5001 | 5003 | 24960 | 90220 |
| Pore volume at pore diameter of 5000 nm or less (mercury intrusion method) (cc/g) | 0.71 | 0.55 | 0.45 | 0.04 | 0.64 | 0.64 | 0.50 | 0.21 |
| Pore volume at pore diameter of 5000 nm or more (mercury intrusion method) (cc/g) | 0.93 | 0.69 | 0.64 | 0.38 | 0.45 | 0.45 | 0.48 | 0.52 |
| BET specific surface area (m$^2$/g) | 19.5 | 4.6 | 2.8 | 0.4 | 1.0 | 2.2 | 17.8 | 4.9 |
| Average pore diameter (gas adsorption method) (nm) | 3.3 | 9.2 | 11.0 | 31.5 | 16.7 | 10.1 | 55.2 | 11.0 |
| Pore volume (gas adsorption method) (cc/g) | 0.160 | 0.011 | 0.008 | 0.003 | 0.004 | 0.006 | 0.246 | 0.013 |
| Spray test result | | | | | | | | |
| Adhesive strength (MPa) | 12.0 | 11.9 | 11.2 | — | Spraying was impossible | Spraying was impossible | 11.6 | 9.5 |
| Cross-sectional hardness (HV0.3) | 123 | 142 | 148 | — | | | 162 | 111 |
| Film thickness (μm) | 140 | 160 | 150 | — | | | 160 | 150 |
| Surface roughness (Ra, μm) | 8.4 | 7.7 | 8.1 | — | | | 8.9 | 8.1 |
| Film forming speed (μm/pass) | 23 | 20 | 32 | — | | | 16 | 25 |

The invention claimed is:

1. A plasma spray material, comprising a hydroxyapatite powder having a mode diameter of 550 to 1000 nm at a pore diameter of 5000 nm or less measured by a mercury intrusion method.

2. The plasma spray material according to claim 1, wherein the mode diameter is 550 to 750 nm.

3. The plasma spray material according to claim 1, wherein the hydroxyapatite powder has a bulk density of 0.6 g/mL or more.

4. The plasma spray material according to claim 1, wherein the hydroxyapatite powder has a bulk density of 0.7 to 1 g/mL.

5. The plasma spray material according to claim 1, wherein the hydroxyapatite powder has a pore diameter of 5000 nm or more measured by the mercury intrusion method.

6. The plasma spray material according to claim 1, wherein the hydroxyapatite powder has a pore diameter of 20000 to 50000 nm measured by the mercury intrusion method.

7. The plasma spray material according to claim 1, wherein the hydroxyapatite powder has a pore volume of 0.01 to 0.5 cc/g at a pore diameter of 5000 nm or less measured by the mercury intrusion method.

8. The plasma spray material according to claim 1, wherein an average particle diameter (particle diameter at which a cumulative degree is 50%) of the hydroxyapatite powder measured using a laser diffraction/scattering particle size distribution analyzer is more than 30 to 350 μm.

9. The plasma spray material according to claim 1, wherein in a particle size distribution of the hydroxyapatite powder measured using a laser diffraction/scattering particle size distribution analyzer, a particle diameter (D10) at which the cumulative degree is 10% satisfies 45 to 75 μm, a particle diameter (D50) at which the cumulative degree is 50% satisfies 80 to 120 μm, and a particle diameter (D90) at which the cumulative degree is 90% satisfies 130 to 170 μm.

10. A system for forming a hydroxyapatite film on a substrate, the system comprising a plasma spray material according to claim 1 and a plasma spraying device.

11. The system according to claim 10, wherein the substrate is a metal substrate.

12. The system according to claim 11, wherein the metal substrate contains a titanium alloy.

13. The system according to claim 11, wherein the metal substrate is an artificial joint.

14. A method of forming a hydroxyapatite film, comprising plasma-spraying the plasma spray material according to claim 1 to form a hydroxyapatite film on a substrate.

15. The method of forming a hydroxyapatite film according to claim 14, wherein the substrate is a metal substrate.

16. The method of forming a hydroxyapatite film according to claim 15, wherein the metal substrate contains a titanium alloy.

17. The method of forming a hydroxyapatite film according to claim 15, wherein the metal substrate is an artificial joint.

* * * * *